(12) United States Patent
Sumida et al.

(10) Patent No.: US 7,998,712 B2
(45) Date of Patent: Aug. 16, 2011

(54) PROCESS FOR PRODUCTION OF TRANSESTERIFIED OILS/FATS OR TRIGLYCERIDES

(75) Inventors: Motoo Sumida, Uji (JP); Kenichi Higashiyama, Kobe (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 1007 days.

(21) Appl. No.: 10/527,703

(22) PCT Filed: Sep. 12, 2003

(86) PCT No.: PCT/JP03/11744
§ 371 (c)(1),
(2), (4) Date: Oct. 13, 2005

(87) PCT Pub. No.: WO2004/024930
PCT Pub. Date: Mar. 25, 2004

(65) Prior Publication Data
US 2006/0141592 A1 Jun. 29, 2006

(30) Foreign Application Priority Data

Sep. 13, 2002 (JP) .................................. 2002-268720

(51) Int. Cl.
*C12P 7/64* (2006.01)
*A61K 1/17* (2006.01)
(52) U.S. Cl. ............. 435/134; 424/442; 426/35; 426/54
(58) Field of Classification Search ........................ None
See application file for complete search history.

(56) References Cited

U.S. PATENT DOCUMENTS

| 4,268,527 | A | 5/1981 | Matsuo et al. |
| 5,204,250 | A | 4/1993 | Shinmen et al. |
| 5,658,767 | A | 8/1997 | Kyle |
| 6,117,905 | A | 9/2000 | Higashiyama et al. |
| 6,369,252 | B1 | 4/2002 | Akoh |
| 7,538,238 | B2 | 5/2009 | Akimoto et al. |

FOREIGN PATENT DOCUMENTS

| EP | 0 223 960 A2 | 6/1987 |
| EP | 0 276 541 A2 | 8/1988 |
| EP | 0 466 375 A1 | 1/1992 |
| EP | 0 956 774 A1 | 11/1999 |
| EP | 0 965 578 A1 | 12/1999 |
| EP | 0 568 608 B1 | 9/2000 |
| EP | 1 411 129 A1 | 4/2004 |
| JP | 55-71797 | 5/1980 |
| JP | 58-042697 | 3/1983 |
| JP | 63-012290 | 1/1988 |
| JP | 63-044891 | 2/1988 |
| JP | 4-273888 | 9/1992 |
| JP | 06 287593 | 10/1994 |
| JP | 08 214891 | 8/1996 |
| JP | 10-191886 | 7/1998 |
| JP | 10 290699 | 11/1998 |
| JP | 11-151075 | 6/1999 |
| JP | 2000 004894 | 1/2000 |
| WO | WO 03/004667 A1 | 1/2003 |

OTHER PUBLICATIONS

Office Action issued Mar. 17, 2008, in European Patent Application No. 03 795 438.5-1212.
Jensen, "The Lipids in Human Milk," Prog. Lipid Res., vol. 35, No. 1, pp. 53-92, 1996.
Liu et al., "In Vitro Hydrolysis of Fungal Oils: Distribution of Arachidonic Acid-Containing Triacylglycerol Molecular Species," JAOCS, vol. 75, No. 4, pp. 507-510, 1998.
Gill et al., "Lipid Accumulation in an Oleaginous Yeast (*Candida* 107) Growing on Glucose in Single-Stage Continuous Culture," Applied and Environmental Microbiology, vol. 38, No. 2, pp. 231-239, Feb. 1977, American Society for Microbiology, Washington, DC.
Kendrick et al., "Lipids of Selected Molds Grown for Production of n-3 and n-6 Polyunsaturated Fatty Acids," Lipids, vol. 27, No. 1, pp. 15-20, 1992.
Office Action issued Jan. 12, 2009, in Taiwan Patent Application No. 092125255, filed Sep. 12, 2003 (with English-language translation).
International Search Report issued Apr. 23, 2004 in PCT/JP03/11744 filed Sep. 12, 2003.
Tane K et al., "Preparation of Polyunsaturated Oil by Repeated Transesterification with Lipase", Yukagaku—Journal of Japan Oil Chemists' Society, Nihon Yukagaku Kyokai, Tokyo, Japan, 1997, pp. 785-790 vol. 46, No. 7.
Office Action issued by European Patent Office in European Application No. 03 795 438.5-1212 dated May 25, 2009.
Shimada et al., "Enzymatic Synthesis of Structured Lipid Containing Arachidonic and Palmitic Acids," JAOCS, vol. 77, No. 1 (2000), pp. 359-363.
Shimada et al., "Production of Functional Lipids Containing Polyunsaturated Fatty Acids with Lipase," in Methods in Lipid Modification, Bornscheuer, ed., Wiley-VCH Verlag GmbH & Co., Weinheim, FRG, Chapter 8 (2000), pp. 128-147.
Fujimoto et al., Science and Industry, 2001, No. 75, pp. 53-60.
Office Action issued in corresponding JP Application No. 2004-535969, dated Oct. 20, 2009.
Christie, W. W., "The positional distribution of fatty acids in triglycerides" in Analysis of oils and fats, Edited by Hamilton, R. J. and Russell, J. B., pp. 313-339, Elsevier Applied Science, London (1986).
Higashiyama, K. et al., "Enhancement of arachidonic acid production by *Mortierella alpina* 1S-4 ," J. Am. Oil Chem. Soc., vol. 75, No. 11, pp. 1501-1505, 1998.
European Office Action issued Nov. 15, 2010 in European Application No. 03 795 438.5.
Osborn et al., "Structured Lipids-Novel Fats with Medical, Nutraceutical, and Food Applications," Comprehensive Reviews in Food Science and Food Safety, vol. 3, 2002, pp. 110-120.

*Primary Examiner* — Herbert J. Lilling
(74) *Attorney, Agent, or Firm* — Drinker Biddle & Reath LLP

(57) ABSTRACT

There are provided polyunsaturated fatty acids-containing oils/fats or triglycerides with high digestion and absorption properties and resistance to oxidative damage, which are suitable for applications in fields such as modified milk for infants, food products and healthy foods and/or supplements, produced by transesterification of polyunsaturated fatty acids-containing oils/fats or triglycerides with vegetable oils/fats or triglycerides using 1,3-position specific type lipases.

10 Claims, 1 Drawing Sheet

PROCESS FOR PRODUCTION OF TRANSESTERIFIED OILS/FATS OR TRIGLYCERIDES

TECHNICAL FIELD

The present invention relates to a method of improving microbe-produced oils/fats or triglycerides which comprise polyunsaturated fatty acids as constituent fatty acids, by lipase transesterification, as well as to improved oils/fats or triglycerides and to human nutritive compositions comprising the improved oils/fats.

BACKGROUND ART

Eicosapentaenoic acid (hereinafter referred to as "EPA") and docosahexaenoic acid (hereinafter referred to as "DHA") are the polyunsaturated fatty acids known in particular for their numerous physiological functions, including preventive effects against adult diseases such as arteriosclerosis and thrombosis, anticancer effects and learning reinforcement effects, and they are often utilized in drugs and special healthy foods and/or supplements. Recently, however, the physiological functions of other polyunsaturated fatty acids have been the subject of increasing attention.

Arachidonic acid is one of these polyunsaturated fatty acids and constitutes approximately 10% of the fatty acids composing important organs such as the blood and liver (for example, the compositional ratio of fatty acids in human blood phospholipids is 11% arachidonic acid, 1% eicosapentaenoic acid and 3% docosahexaenoic acid). As a major constituent of cell membranes it is involved in regulating membrane fluidity, and performs various roles in biometabolism while also serving as an important direct precursor to prostaglandins. A recent area of attention has been the role of arachidonic acid as an infant nutrient and its presence as a constituent fatty acid of endogenous cannabinoids (2-arachidonoyl monoglycerol, anandamide) which exhibit a neurostimulating action. Consumption of linoleic acid-rich foods usually results in conversion to arachidonic acid, but direct ingestion of arachidonic acid in the form of triglycerides is preferred because of a reduced function of the enzymes involved in biosynthesis in adult disease patients and those at risk, infants and the elderly who, as a result, tend to be deficient in arachidonic acid.

Fish oil is an abundant source of EPA and DHA, but dihomo-γ-linolenic acid, arachidonic acid and 4,7,10,13,16-docosapentaenoic acid (22:5 ω6) are almost unobtainable from conventional oil and fat sources. At the current time, it is common to use oils/fats or triglycerides whose constituent fatty acids are polyunsaturated fatty acids and which are obtained by fermentation with microbes. For example, according to one proposed method, various microbes capable of producing oils/fats or triglycerides containing arachidonic acid as the constituent fatty acid are cultured to yield the oils/fats or triglycerides containing arachidonic acid as the constituent fatty acid. Such methods include those for obtaining arachidonic acid-rich oils/fats or triglycerides using fungi of the genus *Mortierella* (see, for example, Japanese Unexamined Patent Publication No. 63-44891 and Japanese Unexamined Patent Publication No. 63-12290). Triglycerides containing fermentation-produced arachidonic acid as the constituent fatty acid are used for purposes requiring arachidonic acid, such as in the field of infant nutrition and, particularly, in modified milk.

Methods of adding arachidonic acid-containing oils or fats to modified milk have been disclosed in the field of infant nutrition (see Japanese Unexamined Patent Publication No. 11-151075, Japanese Unexamined Patent Publication No. 10-191886). The arachidonic acid-containing oils or fats used as additives are produced by fungi, and from a molecular standpoint are characterized by comprising 6-24% AAA (a triglyceride with 3 residues of arachidonic acid in the molecule). A higher arachidonic acid content is known to result in a higher AAA concentration (see, for example, Jim-Wen Liu et al., In vitro hydrolysis of fungal oils: distribution of arachidonic acid-containing triacylglycerol molecular species, J. Am. Oil Chem. Soc., 75, pp. 507-510(1998)).

Oils and fats containing a high concentration of AAA differ from vegetable oils and fats in being resistant to the action of human digestive enzymes (pancreatic lipases) under physiological conditions and, therefore, such oils and fats are not readily digested and absorbed by infants or elderly with low pancreatic lipase activity (see, for example, Jim-Wen Liu et al.).

As the arachidonic acid content of human breast milk is 0.5% of the total fatty acids (see, for example, Christie, W. W., "The positional distribution of fatty acids in triglycerides" in Analysis of oils and fats, Edited by Hamilton, R. J. and Russell, J. B., pp. 313-339, Elsevier Applied Science, London (1986)), presumably there is a higher probability of one arachidonic acid residue per triglyceride molecule rather than greater arachidonic acid condensation per molecule as in AAA described above. Consequently, addition of arachidonic acid-containing oils and fats obtained by fermentation with fungi to modified milk simply on the basis of the fatty acid content is not desirable.

Many attempts have been made to enzymatically alter oils and fats to enhance their properties (solubility in the mouth, crystallinity, heat resistance). Most have involved enzymatic modification of vegetable oils or fats, such as enzymatic synthesis of cacao substitute oils (see, for example, Japanese Unexamined Patent Publication No. 55-71797, Japanese Unexamined Patent Publication No. 58-42697). The production technology disclosed here is for vegetable oils and fats that exhibit high lipase reactivity, whereas oils and fats rich in polyunsaturated fatty acids with poor reactivity are poorly suitable in terms of lipase reactivity.

Oils/fats or triglycerides rich in polyunsaturated fatty acids have not been used for enzymatic modification because of their poor enzyme reactivity, but it has been attempted to produce lipids with polyunsaturated fatty acids structure using medium-chain fatty acid- and polyunsaturated fatty acids-rich oils and fats, by using altered immobilized enzymes (see Japanese Unexamined Patent Publication No. 8-214891, PCT/JP02-06702). According to this method, the fatty acid at the 1- and/or 3-positions of the triglyceride are replaced with octanoic acid, thereby releasing the free polyunsaturated fatty acids. Polyunsaturated fatty acids-rich oils or fats are therefore not expected products. Another disadvantage is that further purification techniques such as precision distillation and the like are required to remove the free fatty acids.

Fujimoto et al. have studied in detail the effects of oil/fat structure on the oxidative stability of polyunsaturated fatty acids, in light of the fact that fish oils (particularly oils rich in EPA and DHA) readily oxidize and adequate oxidative stability cannot be achieved with addition of antioxidants (see, for example, Fujimoto, K., "Effects of oil and fat structure on oxidation stability of polyunsaturated fatty acids", Science and Industry, 75, pp. 53-60, Osaka Industrial Research Association (2001)). An improvement in oxidative stability was discovered by adding special fats (C8 and C14 triglycerides of medium chain fatty acids) to sardine oil (rich in polyunsaturated fatty acids) and conducting transesterification with position non-specific type lipases, and upon examining the ease of oxidation of the chemically synthesized polyunsaturated fatty acids triglyceride EEE (tri-EPA), and comparing types with the polyunsaturated fatty acids dispersed among the molecules and with a higher condensation in the same molecule, the dispersed type was confirmed to be satisfactory.

Transesterification has been disclosed as a method of stabilizing oils and fats in order to prevent oxidation of polyunsaturated fatty acids in fish oils and the like (see Japanese Unexamined Patent Publication No. 6-287593). However, the polyunsaturated fatty acids in fish oils and the like have low reactivity for the lipases used in transesterification reactions. According to this method, therefore, vegetable oils or fats with high lipase reactivity are used in a large amount to dilute one or more polyunsaturated fatty acids-containing oils purified from fish oil or the like in order to ensure lipase reactivity. As a result, it is not possible to achieve an increased content of polyunsaturated fatty acids in the stabilized oils and fats.

DISCLOSURE OF INVENTION

It has therefore been a desired goal to provide oils/fats or triglycerides containing polyunsaturated fatty acids which can be applied in the fields of modified milk for infants, food products and healthy foods and/or supplements, and which exhibit properties such as ready digestion and absorption and resistance to oxidative damage. In order to achieve this goal, the present invention provides a method of improving oils/fats or triglycerides containing polyunsaturated fatty acids such as arachidonic acid by lipase transesterification reaction in order to produce oils and fats with dispersed polyunsaturated fatty acids, as well as compositions comprising them and food products or healthy foods and/or supplements containing them.

Polyunsaturated fatty acids-rich oils/fats or triglycerides having high polyunsaturated fatty acids contents and exhibiting high digestion and absorption properties as well as resistance to oxidative damage were successfully obtained by transesterification of 50-100 parts by weight of one or more oils/fats or triglycerides containing at least 20% of fungus-produced polyunsaturated fatty acids containing 20 or more carbons and two or more double bonds and 0-50 parts by weight of one or more vegetable oils/fats or triglycerides, in a deoxygenated state using a 1,3-position specific type lipase, with an increased reaction temperature.

DETAILED DESCRIPTION OF THE INVENTION

Figure 1:
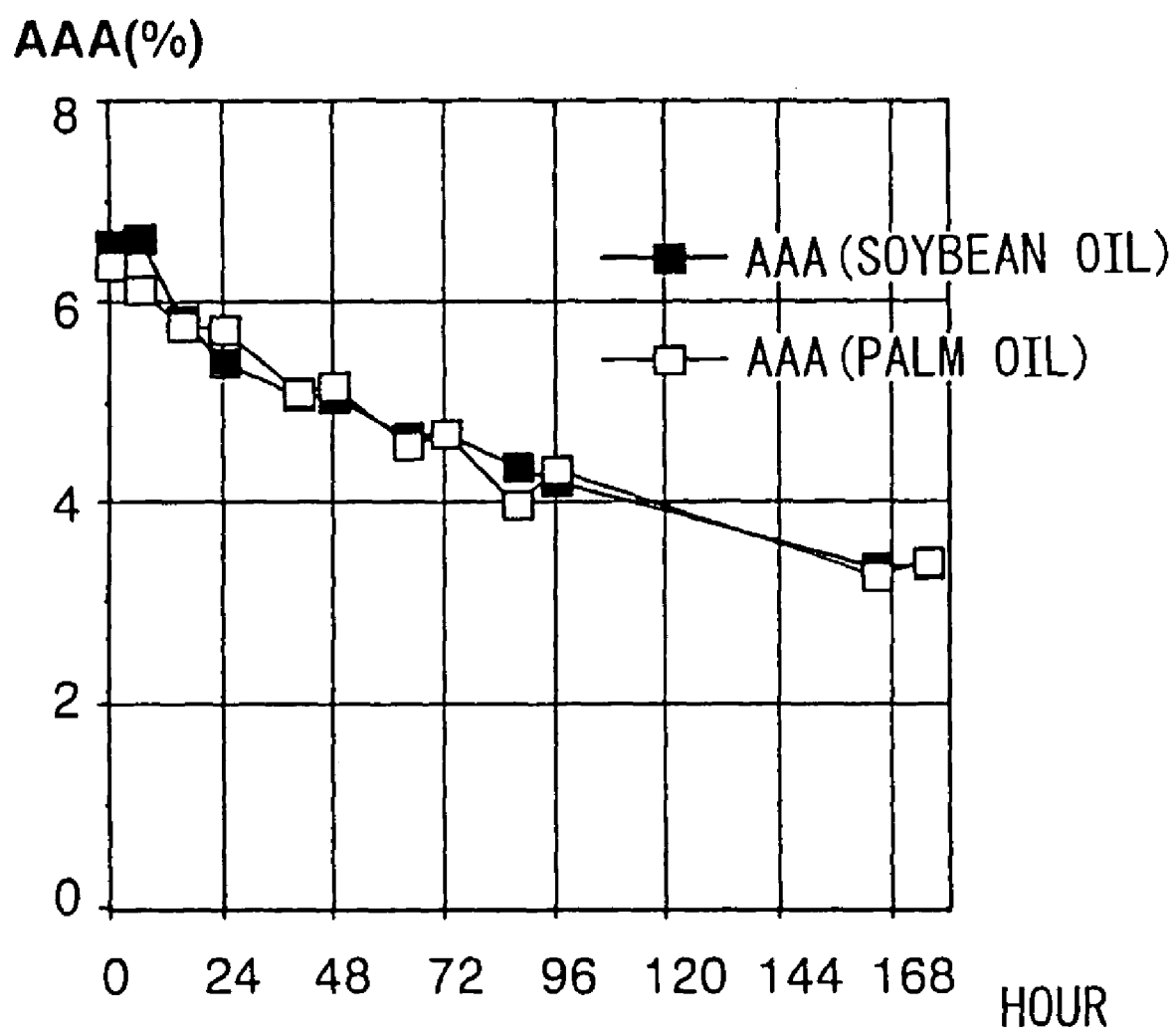
FIG. 1 is a graph showing the effects of palm oil and soybean oil on reduction of triarachidonic acid triglyceride (AAA) in a transesterification reaction.

Specifically, the present invention provides a method suitable for commercial production of oils and fats converted by transesterification reaction, which has been accomplished by:

discovering a method whereby an immobilized enzyme may be used to increase thermal stability and allow use of the enzyme at a high reaction temperature, while oxygen in the immobilized enzyme itself may be removed to avoid oxidative damage of the raw material/reacting oil during the reaction at high temperature, thus preventing oxidative damage and accomplishing a practical enzyme reaction; and discovering a method whereby moisture used for activation of the enzyme may be efficiently eliminated after activation of the enzyme to minimize the amount of free fatty acids, monoglycerides and diglycerides which are secondarily produced as the transesterification reaction occurs with an equilibrium between hydrolysis and ester synthesis reactions, thus accomplishing a practical enzyme reaction.

The invention therefore provides a method for producing edible transesterified oils and fats obtained by lipase transesterification reaction using fungus-produced polyunsaturated fatty acids-containing oils/fats or triglycerides as raw materials, as well as compositions containing the oils and fats.

Since the arachidonic acid content of breast milk lipid is less than 1 wt %, it is assumed that at most only one arachidonic acid residue is present in each triglyceride molecule. The molecular species in an arachidonic acid-rich oils/fats produced by fermentation of a fungus belonging to the genus *Mortierella* (SUNTGA40S: trade name of Suntory Co., Ltd.) are listed in Table 1.

TABLE 1

| Forms of arachidonic acid in SUNTGA40S | |
| --- | --- |
| Molecular species | Content (wt %) |
| AAA | 10.57 |
| XAA | 37.56 |
| XXA | 26.52 |
| XXX | 25.35 |

Here, A represents arachidonic acid bound to the triglyceride, and X represents a fatty acid other than arachidonic acid bound to the triglyceride. Specifically, "AAA" represents a triglyceride with 3 arachidonic acid residues in the molecule, "XAA" represents a triglyceride with 2 arachidonic acid residues and a residue of a fatty acid other than arachidonic acid, and "XXA" represents a triglyceride with 1 arachidonic acid residue and two residues of a fatty acid other than arachidonic acid. Triglycerides containing arachidonic acid constitute 74.7% of the total triglycerides, but this consisted of 26.52% XXA which is presumed to be present in breast milk, and 48% of AAA or XAA which are believed to be not present. It is thought that a form of arachidonic acid close to that in breast milk can be obtained by converting the 48% of AAA and XAA to the form of XXA.

The present inventors attempted to produce transesterified oils and fats with relatively low amounts of vegetable oils and fats using 1,3-position specific type lipases in a deoxygenated state for the purpose of improving the aforementioned fungal arachidonic acid-rich oils/fats and triglycerides produced by fermentation. As a result the inventors succeeded in dispersing arachidonic acid bound at 1- and 3-positions of a raw material AAA trigriceride which is abundant in fungal arachidonic acid oils and fats and is not digested or absorbed, while also approximating the structural form of human breast milk (XXA).

The oils and fats modified by the present transesterification method may be utilized for a wide range of purposes including addition to modified milks in the field of infant nutrition, as well as for food products and healthy foods and/or supplements. Methods of enzyme activation and oxygen removal Methods of improving oils and fats by enzymatic transesterification have long been implemented and are described in prior art documents. The present arachidonic acid-rich oils and fats include many arachidonic acid residues such as AAA which do not readily function under physiological lipase reaction conditions, and this has constituted a problem for enzyme reactivity in transesterification. For increased transesterification efficiency it is desirable to improve the esterexchange rate by immobilizing the lipase and conferring heat resistance for an increased reaction temperature (see, for example, Japanese Unexamined Patent Publication No. 8-214891, PCT/JP02-06702). However, when the reaction is conducted at high temperature to improve the reaction efficiency, the arachidonic acid-rich oils or fats as the raw material tends to undergo oxidative damage. Particularly when an immobilized enzyme is used, a problem is posed by removal of oxygen which has penetrated into the immobilizing resin. The present inventors therefore discovered a method for efficiently removing oxygen from the immobilized enzyme and developed a method for transesterification under low-oxygen conditions.

The POV (peroxide value) is widely used as a parameter indicating the degree of oxidative damage of oils or fats. The amount of oxygen in the reaction system was varied for the transesterification reaction and the degree of oxidative damage of the oils or fats was compared by measuring the POV. The amount of oxygen was adjusted on the following 4 levels: Highest deoxygenation level="deairing and nitrogen blow", Level with nitrogen substitution by ordinary nitrogen blow="nitrogen blow", Level with absolutely no nitrogen substitution of reaction vessel="no nitrogen substitution", Final use of only an immobilized enzyme support for control to a non-nitrogen substituted condition="controlled". The POV values were measured after reaction for a prescribed period at temperatures of 30° C., 45° C. and 55° C. As shown in Table 2, the POV rises in direct proportion to the amount of residual oxygen and, particularly, as the POV rose with increasing reaction temperature in the "nitrogen blow" deairing condition at the level with nitrogen substitution by ordinary nitrogen blow, removal of oxygen was thought to be insufficient. This means that reaction under this condition cannot prevent deterioration of the oils or fats, and these results revealed that the POV increase can be suppressed by increasing the deoxygenation to the next level of "deairing and nitrogen blow" to obtain oils or fats of sufficient quality.

TABLE 2

POV with reaction under different conditions

|  | 30° C., 1 day | 45° C., 3 days | 55° C., 1 day |
| --- | --- | --- | --- |
| Deairing and nitrogen blow | 0.87 | 0.88 | 0.87 |
| Nitrogen blow | 1.07 | 1.23 | 2.75 |
| No nitrogen substitution | 1.28 | 1.86 | 3.15 |
| Controlled | 2.69 | 4.50 | 4.05 |

(POV: meq/kg oil/fat)

In the case of *Rhizopus delemar* (current name: *Rhizopus oryzae*) lipase, a small amount of moisture (approximately 2%) must be added for enzyme activation. This necessitates a procedure for eliminating the excess moisture in the activated immobilized enzyme. This procedure must also be accompanied by a procedure for deoxygenation, which can be carried out simultaneously with the enzyme activation or moisture elimination. At the enzyme activation stage, the oil or fat raw material and a small amount of water are added to the immobilized enzyme and reaction is conducted at 30-45° C. for about one day for enzyme activation. For simple activation of the immobilized enzyme, an inexpensive vegetable oil or fat may be used instead of an expensive polyunsaturated fatty acids-containing oil or fat. The oxygen removal may be accomplished either during or before the stage of adding the moisture-containing oil or fat raw material to the immobilized enzyme, using a vacuum device such as a vacuum pump for deairing of the oil or fat raw material and immobilized enzyme, and allowing leakage of nitrogen gas instead of air when the pressure is restored to ordinary pressure. The oxygen in the immobilized enzyme can be removed out by repeating this vacuum/pressure restoration procedure. After completion of the activation reaction, the oil or fat is removed, and the oxygen is eliminated from the oil/fat-absorbed immobilized enzyme by further repeating the aforementioned vacuum/nitrogen gas leakage procedure. The oxygen-eliminated (nitrogen-substituted) oil/fat raw material is then added for transesterification, which can be accomplished while preventing oxidative damage of the oil or fat even under high temperature conditions.

Method of Eliminating Moisture Used for Enzyme Activation or Eliminating Enzyme Present in Enzyme The excess moisture must be eliminated from the immobilized enzyme activated in the aforementioned procedure. The presence of excess moisture promotes hydrolysis by lipases and results in secondary production of diglycerides, monoglycerides and free fatty acids during the transesterification reaction. It is necessary to remove the moisture from the reaction system to prevent such production. The excess moisture can be eliminated by removing the oil/fat used for activation from the activated immobilized enzyme, washing once with the oil/fat of the reaction raw material (oil or fat which has been already deoxygenated or dehydrated) and then reacting it with the crude oil/fat at 45° C. for one day. This subsequent reaction yields a transesterified oil or fat with a low amount of diglycerides, etc. If the purpose is to lower the production cost, an economical vegetable oil or fat such as palm oil may be used instead of an expensive polyunsaturated fatty acids-containing oil or fat for the activation and moisture-eliminating reaction.

While enzyme activation with water has been necessary in the case of immobilizing enzymes of *R. delemar*, a commercially available immobilized enzyme (the *Rhizomucor miehei* lipase Chirazyme L-9, c.-f., C2, lyo, product of Berlinger Mannheim) requires no activation with water but is in an active state due to the trace amount of water present in the immobilized enzyme. However, excess moisture is also included in this immobilized enzyme, and therefore the moisture must be eliminated as in the case of *R. delemar*. The method used for moisture elimination may be the one described above, and no special procedures are required. The elimination of oxygen may also be carried out in the dehydration step for this enzyme as well.

Reactor for Enzyme Reaction

The enzyme reaction has been explained above based on transesterification in a batch system.

A column system is an alternative to a batch system as the method for transesterification of one or more oils or fats using an immobilized enzyme. Specifically, the immobilized enzyme is packed into a column-type jacketed container, the oil or fat raw material is introduced into the column while incubating or heating to adjust the column temperature, and the transesterified oil/fat is taken out from the outlet. In some cases, the oil/fat may be circulated while being passed through the column to increase the conversion rate. Here, the oil/fat raw material may be passed through the column during activation or moisture elimination to expose the immobilized enzyme in the interior to the oil, in combination with vacuum deairing and forced nitrogen gas blow to eliminate the oxygen. The oil or fat may be transesterified after activation and removal of the moisture.

Oil/Fat Raw Material for Transesterification

When one or more oils/fats or triglycerides comprising polyunsaturated fatty acids as a constituent fatty acid are mixed at 50-100 parts by weight with 0-50 parts by weight of one or more vegetable oils/fats or triglycerides, a homogeneous liquid oil or fat is obtained and transesterification with an oxygen-eliminated immobilized enzyme as has been hitherto described may be carried out to obtain a modified oil or fat containing polyunsaturated fatty acids.

<Vegetable Oils/Fats>

The vegetable oil or fat raw material used for the reaction may be one commonly used in foods. The vegetable oils and fats used may also be converted oils and fats. Such vegetable oils and fats are used as sources of saturated fatty acids for transesterification. As examples there may be mentioned linolic acid-rich oils such as soybean oil, safflower oil, olive oil, rice bran oil, sesame oil and the like, oleic/linolic acid-rich oils and saturated fatty acid-rich oils such as palm oil, palm kernel oil, cacao oil, coconut oil, lard oil and the like, and oils obtained by conversion from triglyceride vegetable oils such as MCTs (triglycerides comprising saturated medium-chain fatty acids of 8 carbons and saturated medium-chain fatty acids of 10 carbons, and composed of the same or different fatty acids). Saturated fatty acid-rich oils and fats are preferred for resistance to oxidation and for greater approximation to breast milk components.

When vegetable oils and fats used as sources of saturated fatty acids for transesterification are compared, such as saturated fatty acid-rich palm oil and relatively unsaturated fatty acid-rich soybean oil, the rate of reduction of AAA during transesterification is roughly the same for both oils, with no difference in the AAA content seen, and therefore it is believed that these exhibit an improving effect toward a more highly digestible and absorbable oil/fat. However, some difference is found in the resistance against oxidative damage due to differences in the fatty acids introduced by the transesterification reaction.

MCT, in particular triglycerides containing octanoic acid as a constituent fatty acid, and microbial arachidonic acid triglycerides are transesterified by a lipase according to the present invention to produce triglycerides containing arachidonic acid as a constituent fatty acid, such as "8A8", "88A". This method is useful for producing oils and fats containing arachidonic acid economically without waste of arachidonic acid, and arachidonic acid-containing oils and fats resulting therefrom are useful as novel oils and fats having improved digestibility and absorbability.

There may also be mentioned oils and fats separated from these oils and fats or having increased saturated fatty acid contents by partial hydrogenation, although the usable oils and fats are not limited to these.

<Oils/Fats Comprising Polyunsaturated Fatty Acids as Constituent Fatty Acids>

It is essential to culture microbes capable of producing the oils/fats or triglyceride containing the polyunsaturated fatty acids as a constituent fatty acid. Here, the microbes are preferably microbes that produce at least one type of ω6, ω9 or ω3 series polyunsaturated fatty acids having 20 or more carbons and 2 or more double bonds, primarily as a triglyceride constituent fatty acid.

As ω6, ω9 or ω3 series polyunsaturated fatty acids having 20 or more carbons and 2 or more double bonds there may be mentioned dihomo-γ-linolenic acid (8,11,14-eicosatrienoic acid:DGLA), arachidonic acid (5,8,11,14-eicosatetraenoic acid), 7,10,13,16-docosatetraenoic acid (22:4 ω6), DPA ω6 (4,7,10,13,16-docosapentaenoic acid), 8,11-eicosadienoic acid, mead acid (5,8,11-eicosatrienoic acid), 8,11,14,17-eicosatetraenoic acid (20:4 ω3), EPA (5,8,11,14,17-eicosapentaenoic acid), DPA ω3 (7,10,13,16,19-docosapentaenoic acid) and DHA (4,7,10,13,16,19-docosahexaenoic acid).

According to the present invention, therefore, any microbe may be used which can produce an oil/fat or triglyceride containing polyunsaturated fatty acids as a constituent fatty acid. As examples of microbes capable of producing oils/fats or triglycerides containing arachidonic acid as a constituent fatty acid there may be mentioned microbes belonging to the genus *Mortierella, Conidiobolus, Pythium, Phytophthora, Penicillium, Cladosporium, Mucor, Fusarium, Aspergillus, Rhodotorula, Entomophthora, Echinosporangium* or *Saprolegnia*. As microbes belonging to the genus *Mortierella* subgenus *Mortierella* there may be mentioned *Mortierella elongata, Mortierella exigua, Mortierella hygrophila, Mortierella alpina*, and the like. Specifically, there may be mentioned strains such as *Mortierella elongata* IFO8570, *Mortierella exigua* IFO8571, *Mortierella hygrophila* IFO5941, *Mortierella alpina* IFO8568, ATCC16266, ATCC32221, ATCC42430, CBS219.35, CBS224.37, CBS250.53, CBS343.66, CBS527.72, CBS529.72, CBS608.70, CBS754.68, etc. As examples of DHA-producing microbes there may be mentioned those belonging to the genuses *Crypthecodenium, Thrautochytrium, Schizochytrium, Ulkenia, Japonochytrium, Haliphthoros*, and the like.

These strains are all available without restriction from the Institute for Fermentation, Osaka (IFO), the American Type Culture Collection (ATCC) and the Centralbureau voor Schimmelcultures (CBS). In addition, there may be used strain *Mortierella elongata* SAM0219 (FERM P-8703) (FERM BP-1239) separated from soil by the research group of the present inventors.

For culturing of the strains used for the invention, the spores, hypha or seed culture solution obtained by preculturing or cells collected from the seed culture solution are inocultured to liquid or solid medium for main culturing. In the case of a liquid medium, the carbon source used may be any commonly used one such as glucose, fructose, xylose, saccharose, maltose, solubilized starch, molasses, glycerol, mannitol or saccharized starch, although there is no limitation to these. As nitrogen sources there may be used organic nitrogen sources, including natural nitrogen sources such as peptone, yeast extract, malt extract, meat extract, casamino acid, corn steep liquor, soybean protein, defatted soybean, cottonseed meal or the like, as well as urea, and inorganic nitrogen sources such as sodium nitrate, ammonium nitrate and ammonium sulfate, and in particular there may be mentioned soybean-derived nitrogen sources such as soybean, defatted soybean, soybean flakes, edible soybean protein, okara (beancurd refuse), soybean milk, parched soybean flour and the like. More particularly there may be used one or more types of heat denatured defatted soybean, and more preferably defatted soybean heat treated at about 70-90° C. and removed of its ethanol-soluble components, or combinations with the aforementioned nitrogen sources. If necessary, phosphorus ion, potassium ion, sodium ion, magnesium ion and calcium ion, as well as ions of metals such as iron, copper, zinc, manganese, nickel, cobalt and the like or vitamins may also be used as trace nutrient sources.

These medium components are not particularly restricted so long as they are at concentrations which do not inhibit growth of the microbes. In practice, the carbon source will generally be added in a total amount of 0.1-40 wt % and preferably 1-25 wt %, and the nitrogen source in a total amount of 2-15 wt % and preferably 2-10 wt % and, more preferably, the initial carbon source is added at 1-5 wt % and the initial nitrogen source at 3-8 wt %, after which the carbon and nitrogen source and more preferably only the carbon source is added during the culturing. In order to increase the polyunsaturated fatty acid yield, for example, a hydrocarbon such as hexadecane or octadecane; a fatty acid such as oleic acid or linoleic acid or a salt thereof, or a fatty acid ester such as an ethyl ester, glycerin fatty acid ester or sorbitan fatty acid ester; or an oil such as olive oil, soybean oil, rapeseed oil, cottonseed oil or coconut oil, may be used as an unsaturated fatty acid precursor, either alone or in combinations. The amount of substrate added may be 0.001-10 wt % and preferably 0.5-10 wt % with respect to the medium. Any of these substrates may also be used as the sole carbon source for culturing.

The culturing temperature for the polyunsaturated fatty acids-producing microbe will differ depending on the microbe, but may be 5-40° C. and preferably 20-30° C., or the cells may be cultured at 20-30° C. for growth and the culturing continued at 5-20° C. to produce the unsaturated fatty acid. Such temperature management can also be used to increase the proportion of polyunsaturated fatty acids among the produced fatty acids. The pH of the medium may be 4-10 and preferably 5-9, and the culturing method may be submerged culturing, shake culturing, solid culturing or stationary liquid culturing. The culturing will usually be conducted for 2-30 days, preferably for 5-20 days and more preferably for 5-15 days.

Microbes belonging to the genus *Mortierella* subgenus *Mortierella* are known as microbes capable of producing oils/fats or triglycerides containing arachidonic acid as the main constituent fatty acid but, by mutating the aforementioned strains, the present inventors have obtained microbes capable of producing oils/fats or triglycerides comprising dihomo-γ-linolenic acid as the main constituent fatty acid (see Japanese Unexamined Patent Publication No. 5-91887) and capable of producing oils/fats or triglycerides comprising ω9 series polyunsaturated fatty acids as the main constituent fatty acids (see Japanese Unexamined Patent Publication No. 5-91888). In addition, the inventors have obtained microbes with resistance to high-concentration carbon sources (PCT Patent Publication WO 98/39468) which are microbes belonging to the genus *Mortierella* subgenus *Mortierella*. The present invention, however, is not limited to microbes of the genus *Mortierella* subgenus *Mortierella*, and any microbes capable of producing oils/fats or triglycerides containing polyunsaturated fatty acids as the constituent fatty acids may be used.

As the method of obtaining the crude oil from the microbe cultured in the manner described above, the cultured solution is subjected to ordinary solid/liquid separation means such as natural sedimentation, centrifugal separation and/or filtration, either directly or after a treatment such as sterilization, concentration, acidification or the like, to obtain the cultured cells. A flocculent or filtering aid may also be added to facilitate the solid/liquid separation. As flocculating agents there may be used, for example, aluminum chloride, calcium chloride, algin, chitosan and the like. As filtering aids there may be used, for example, diatomaceous earth. The cultured cells are preferably rinsed, crushed and dried. The drying may be carried out by lyophilization, blow drying, fluidized bed drying or the like. The means for obtaining the crude oil from the dried cells may be extraction with an organic solvent or compression, but preferably extraction is performed with an organic solvent under a nitrogen stream. As organic solvents there may be used ethanol, hexane, methanol, chloroform, dichloromethane, petroleum ether, acetone or the like, and methanol/petroleum ether alternating extraction or chloroform-methanol-water monolayer solvent may also be employed. However, the extraction method used to obtain the crude oil is not limited to these methods, and any method for efficient extraction of oils and fats from cells may be used. For example, supercritical extraction may be employed as an effective means.

The desired crude oil can be obtained by removing the organic solvent or supercritical fluid components from the extract obtained by extraction with an organic solvent or supercritical fluid, under reduced pressure conditions or the like. Extraction may also be performed using wet cells as an alternative to the methods mentioned above. In this case, there is used a water-compatible solvent such as methanol, ethanol or acetone, or a water-compatible mixed solvent comprising such solvents with water and/or another solvent. The procedure is otherwise the same as described above.

A purified oil or fat instead of a crude oil may also be used as the substrate for transesterification. The oil or fat purification step may be accomplished by ordinary methods such as degumming, deacidification, steam distillation, decoloration, column treatment, molecular distillation, wintering or the like.

<Lipases Used for Transesterification>

As examples of lipases to be used for the invention there may be mentioned those produced by microbes belonging to the genus *Rhizopus, Rhizomucor, Aspergillus* or the like, as well as pig pancreatic lipases. Such lipases may be commercially available ones. Examples thereof include *Rhizopus delemar* lipase (Talipase, product of Tanabe Seiyaku) (the current taxonomic classification of *Rhizopus delemar* is *Rhizopus oryzae*), *Rhizopus niveus* lipase (Newlase F3G, product of Amano Enzyme Co., Ltd.) (*Rhizopus niveus* has the same taxonomical classification as *Rhizopus delemar*, both being designated as *Rhizopus oryzae*), *Rhizomucor miehei* lipase (Ribozyme IM by Novo Nordisk Co., Ltd., or Chirazyme L-9, c.-f., C2, lyo, by Berlinger Mannheim) and *Aspergillus niger* lipase (Lipase A, product of Amano Enzyme Co., Ltd.), with no particular limitation to these enzymes, as any 1,3-position specific type lipases may be used.

The form in which the lipase is used is preferably as an immobilized lipase on an immobilizing resin, in order to increase the reaction efficiency for the polyunsaturated fatty acids and to confer stability for repeated use. As immobilizing resins there may be used celite, ion-exchange resins, ceramics, protein-adsorbing adsorption resins and the like. As examples there may be mentioned powdered diatomaceous earth and granular diatomaceous earth as Celite, Dowex MARATHON WBA (Dow Chemical) and DIAION WA30 (Mitsubishi Chemical) as ion-exchange resins, SM-10 (Nihon Gaishi) as a ceramic and DIAION HP20 (Mitsubishi Chemical) as an adsorption resin.

The aforementioned ion-exchange resins, etc. are only examples, and new improved resins are continually being developed and are commercially available. Such improved resins may also be considered suitable for use.

<Reaction Temperature and Time for Transesterification>

The transesterification is preferably conducted at 30-60° C. in consideration of the enzyme reactivity. It is more preferably conducted at 30-50° C. in consideration of stability of the immobilized enzyme when the reaction is carried out continuously using an immobilized enzyme. The time required for the reaction is preferably as short as possible, but the reaction is preferably conducted for 1-7 days in consideration of the XXA or AAA content of the transesterified oil/fat after the reaction. Because the raw material oil and fat (polyunsaturated fatty acids-rich oils and fats) are prone to oxidation during the reaction, oxygen is preferably removed in the manner described above and the reaction is preferably carried out under oxygen-free conditions.

<Purification After Transesterification Reaction>

The oils or fats improved by transesterification in this manner may be easily separated from the immobilized enzyme in the enzyme reactor (whether a column reaction or batch reaction). Most of the components of the prepared oils or fats will be in the form of triglycerides, and these may be purified by ordinary methods used for purification of oils and fats, such as deacidification, degumming, decoloration, steam distillation and the like.

The oils and fats of the invention are improved oils/fats or triglycerides obtained by lipase transesterification of oils/fats or triglycerides comprising microbe-produced polyunsaturated fatty acids as the constituent fatty acids, and they are oils/fats or triglycerides containing at least 20% of polyunsaturated fatty acids containing 20 or more carbons and two or more double bonds, and there may be mentioned transesterified oils/fats or triglycerides containing at least 40% of triglycerides with one residue of polyunsaturated fatty acids containing 20 or more carbons and two or more double bonds in the molecule, and/or no more than 4.0% of triglycerides with 3 residues of the same polyunsaturated fatty acids containing 20 or more carbons and two or more double bonds.

The oils and fats of the invention preferably comprise at least 90% triglycerides. The oils and fats may be any form thereof, but in the present invention, they comprise diglycerides, monoglycerides, and possibly a trace amount of free fatty acids, as resultant products by transesterification, as well as the triglycerides as a major product thereof.

The oils and fats of the invention are, for example, oils/fats or triglycerides containing at least 20% of arachidonic acid, and transesterified oils/fats or triglycerides containing at least 40% of triglycerides with one residue of arachidonic acid in the molecule and/or no more than 4.0% of AAA have unlimited possibilities for use as raw materials and additives in foods, feeds, cosmetics and pharmaceuticals. Furthermore, there are no limitations on the purpose or amounts of their use.

As examples of food compositions there may be mentioned common food products as well as functional foods, nutritional supplements, modified milk for immature infants, modified milk for infants, infant food products, maternal foods or geriatric foods. As examples of food products containing oils or fats there may be mentioned natural foods which naturally contain oils and fats, such as meat, fish and nuts, food products with oils and fats added during preparation, such as soups, food products using oils or fats as heating media, such as donuts, oil or fat food products such as butter, processed food products with oils or fats added during processing, such as cookies, or food products sprayed or coated with oils or fats during final processing, such as hard biscuits. They may also be added to agricultural foods, fermented foods, livestock foods, marine foods or beverages which contain no oils or fats. They may also be in the form of functional food products or pharmaceuticals, and for example, in the form of enteral nutrients, powders, granules, lozenges, oral solutions, suspensions, emulsions, syrups or the like.

The present invention will now be explained in greater detail through the following examples, with the understanding that the invention is in no way restricted by the examples.

EXAMPLES

Example 1

Preparation of Immobilized Enzyme (Conferred Stability and Deoxygenation by Immobilization of 1,3-Specific Lipase)

After suspending 100 g of an ion-exchange resin (Dowex MARATHON WBA: Dow Chemical) in 80 ml of *Rhizopus delemar* lipase solution (12.5% Talipase powder, product of Tanabe Seiyaku), the suspension was dried under reduced pressure to obtain the immobilized enzyme. Next, a triglyceride containing 40% arachidonic acid (SUNTGA40S, trade name of Suntory Co., Ltd.) (25 g), palm oil (15 g), the aforementioned immobilized lipase (4 g) and water (800 μl) were weighed out into a sealable bottle. The half-open bottle was placed in a dessicator, and a vacuum pump was connected to the dessicator for pressure reduction of the contents. (Bubbles were produced in the oil from the immobilized enzyme resin placed in the bottle inside the desiccator together with the oil, thus releasing the air containing the immobilized enzyme.) Nitrogen gas was then leaked into the desiccator to restore the interior of the desiccator to ordinary pressure. This procedure of pressure reduction and restoration was repeated for substitution of nitrogen for the oxygen present in the immobilized resin matrix, and the bottle was sealed. For activation of the immobilized enzyme, the bottle was then shaken (100 rpm) at 30° C. for 24 hours. After completion of activation, the oil used for activation was removed and the deoxygenation procedure was carried out once more to obtain the activated immobilized enzyme. For transesterification with other vegetable oil or fat, the vegetable fat or oil used for transesterification was used instead of palm oil for activation of the immobilized enzyme, in a mixture of the SUNTGA40S (25 g), vegetable oil (15 g), immobilized lipase (2 g) and water (800 μl) as with the palm oil mentioned above, and the aforementioned deoxygenation and immobilized enzyme activation procedures were carried out for transesterification.

Example 2

Method of Measuring Fatty Acid Contents of Oils/Fats

The fat or oil was sampled in an approximately 10-20 mg screw cap test tube, 2 mL of methanolic HCl and 1 mL of dichloromethane were added, the top of the test tube was sealed, and reaction was conducted at 50° C. for 3 hours. After completion of the reaction, the mixture was cooled to room temperature and then hexane was added for extraction of the fatty acid methyl ester and the collected hexane layer was concentrated under reduced pressure. The obtained fatty acid methyl ester was dissolved in hexane to a total fatty acid methyl ester concentration of about 1% and provided for gas chromatography (GC) analysis. The GC analysis conditions and component identification were according to "Fatty Acid Composition by GLC (Method Ce 1b-89)" of Official Methods and Recommended Practices of the AOCS, 5th Edition (American Oil Chemists' Society, 1998), a Supelcowax-10 column was used. The ratio of the arachidonic acid methyl ester peak area with respect to the total peak area detected was recorded as the arachidonic acid content in the oil/fat. The fatty acid contents of fatty acids other than arachidonic acid were determined by the same method.

Example 3

Method of Triglyceride Analysis

HPLC analysis was conducted under the following conditions to measure the content of each triglyceride in the oils or fats modified by the enzyme reaction.

Column: Reverse-phase column (Cosmosil 4.6×250 mm 5C18-MS)
Solvent: Acetone:acetonitrile (1:1) 1 ml/min
Analysis time: 55 min Column oven temperature: 40° C.

Detector: Refractive index detector (cell temperature: 40° C.)

Sample: 5 μl of 10% solution of oil/fat or triglyceride in chloroform

Each triglyceride was analyzed under the above-mentioned measuring conditions. The molecular species of each triglyceride was determined according to the method disclosed in Japanese Unexamined Patent Publication No. 2000-513575. Specifically, the peaks of each triglyceride were separated, and hydrolysis was then followed by methyl ester conversion. The molecular species were determined by GC.

By analyzing the triglycerides of the oils/fats obtained with SUNTGA40S and transesterification by the method described above and performing calculation, it was possible to determine the form of the SUNTGA40S arachidonic acid and the proportion and content of each XXA triglyceride. XXA represents the total weight percentage of LLA, PGA, OLA, PLA, OOA, POA, PPA, SOA, PSA, SSA and LC22A. The notations used here are as follows. L: linoleic acid, P: palmitic acid, G: γ-linolenic acid, O: oleic acid, S: stearic acid, C22: linear saturated $C_{22}$ fatty acid, X: fatty acid other than arachidonic acid, A: arachidonic acid. (The binding positions of each fatty acid residue on the glycerin were not stipulated.)

Example 4

Modification of Arachidonic Acid-Containing Oil/Fat (SUNTGA40S; Approximately 40% as Arachidonic Acid) Using Activated Immobilized Lipase Obtained in Example 1

Enzyme reaction was conducted by shaking (100 rpm) at 30° C. with the raw material composition shown in Table 3 below, and the reaction was continued while sampling to confirm the extent of the transesterification reaction. The AAA conversion was measured by analysis of triglycerides of the sampled oil.

TABLE 3

| Raw material composition for reaction | |
|---|---|
| SUNTGA40S | 25 g |
| Palm oil or soybean oil | 15 g |
| Immobilized lipase | 2 g |

FIG. 1 shows conversion of the AAA content upon combining and transesterifying vegetable oil such as palm oil or soybean oil with arachidonic acid-containing oil as a type of polyunsaturated fatty acids-rich oil/fat or triglyceride. Even transesterification with the saturated fatty acid-rich palm oil resulted in the AAA reduction rate with the unsaturated fatty acid-rich linoleic acid-based soybean oil.

This demonstrated that the rate of AAA disappearance according to the invention is identical regardless of the type of vegetable oil used, so long as the mixing proportion is the same.

Example 5

CDM Test

In order to confirm the oxidative stability of the enzyme-converted arachidonic acid-rich oil, a test sample was prepared and the oxidative stability was measured by a CDM test. The CDM test was conducted by heating the oil sample in a reactor (at constant temperature) while blowing in clean air and capturing in water the volatile decomposition products produced by oxidation. The stability of the oil sample was expressed in terms of the time lapse up to the curve point at which the conductivity of the water changed drastically. A shorter time indicates an oil more susceptible to oxidative damage.

Based on Example 3, a 2-fold amount of the immobilized enzyme (activated) was added (4 g) to the raw material oil (40 g), and reaction was conducted at 30° C., 100 rpm. After the reaction, the oil and immobilized enzyme were separated with a decant to obtain the reaction oil. The AAA content of the obtained oil was analyzed by HPLC and the stability was measured by a CDM test. The reaction time was varied to obtain modified oil 1 and modified oil 2 having different AAA contents.

TABLE 4

AAA contents and stabilities of modified oils (transesterified oils)

| Sample | CDM (hr) | AAA content (%) |
|---|---|---|
| Palm oil/SUNTGA40S | | |
| Modified oil 1 | 6.4 | 3.90 |
| Modified oil 2 | 5.7 | 4.44 |
| Unmodified oil | 4.6 | 6.46 |
| Soybean oil/SUNTGA40S | | |
| Modified oil 1 | 4.1 | 3.69 |
| Modified oil 2 | 3.6 | 4.28 |
| Unmodified oil | 3.5 | 7.01 |

As shown in Table 4, when the saturated fatty acid oil, palm oil, was used as the raw material vegetable oil for reaction, the problematic AAA content was reduced and the stability of the oil against oxidation was increased.

On the other hand, when the linoleic acid oil, soybean oil, was used as the raw material for reaction, a similar reduction in AAA was seen as with palm oil, but the effect on stability as measured by CDM was not as notable as with palm oil.

Example 6

Changes in Components with Time for Transesterification of Arachidonic Acid-Rich Oil (SUNTGA40S) Diluted with Palm Oil The fungus-produced arachidonic acid-rich oil contained abundant AAA, and therefore the AAA was converted to XXA by lipase transesterification reaction in order to approach the form of arachidonic acid (XXA) in breast milk, and the progression and changes in component proportions with time were experimentally measured.

TABLE 5

Changes in triglyceride components with time during transesterification reaction

| Triglyceride component | Time (hr) | | | |
|---|---|---|---|---|
| (%) | 0 hr | 48 hr | 96 hr | 176 hr |
| AAA | 6.37 | 5.16 | 4.33 | 3.41 |
| XAA | 23.19 | 19.09 | 17.00 | 14.86 |
| XXA | 16.11 | 29.33 | 35.41 | 40.55 |

The immobilized enzyme was activated by the method in Example 1, and then 25 g of SUNTGA40S and 15 g of palm oil were added to 2 g of the activated immobilized enzyme and deoxygenation was followed by reaction at 30° C. Sampling was conducted at various times, the triglycerides were analyzed by the method described in Example 2 (HPLC analysis), and each of the component contents were calculated. As shown in Table 5, AAA decreased with time while the presumed conversion product XXA increased. Under these conditions, a period of 1 week was required for approximately ½ reduction of AAA and at least doubling of XXA, from mixing of the oils. The following example was then carried out to determine optimization of the reaction temperature and amount of immobilized enzyme addition.

Example 7

Effect of Reaction Temperature During Transesterification Reaction

The immobilized enzyme prepared in Example 1 was used to examine the effect of the reaction temperature on transesterification. The immobilized enzyme was activated by the method in Example 1, and then 25 g of SUNTGA40S and 15 g of palm oil were added to 2 g of the activated immobilized enzyme and deoxygenation was followed by reaction at different temperatures. The reacted oil was sampled after 1 day of reaction, the triglycerides were analyzed by the method described in Example 2 (HPLC analysis), and the AAA residue was calculated (Table 6).

TABLE 6

Effect of temperature on esterification reaction

| Reaction temperature | AAA residue (%) | AAA reduction (%, per 24 hrs) |
|---|---|---|
| Before reaction | 6.37 | |
| 30° C. | 5.86 | 9% |
| 45° C. | 4.50 | 29% |
| 55° C. | 2.43 | 62% |

Since a transesterification reaction is ordinarily conducted at below 60° C., the reaction was conducted at 30° C., 45° C. and 55° C. and reactivity was confirmed. As shown in the table, the transesterification reaction was confirmed to proceed more efficiently with a higher reaction temperature. The deoxygenation step is therefore important from the standpoint of preventing oxidative damage during reaction at high temperature.

Example 8

Examination with Enzyme Agent Comprising Immobilized *Rhizomucor miehei* Lipase

In the same manner as Example 5, with the enzyme added at 10% and using SUNTGA40S (trade name of Suntory Co., Ltd.) diluted with palm oil, a comparison was made of the transesterification activity of *R. delemar* lipase immobilized and activated according to Example 1, and a commercially available *R. miehei* immobilized lipase (Chirazyme L-9, c.-f., C2, lyo, product of Berlinger Mannheim) which requires no activation with water.

TABLE 7

Comparison of transesterification reactions with *R. delemar* and *R. miehei*

| Molecular species | R. delemar | R. miehei |
|---|---|---|
| AAA | 2.86 | 2.53 |
| XAA | 14.95 | 14.05 |
| XXA | 43.33 | 44.20 |

Each triglyceride was analyzed by the method described in Example 3 (HPLC analysis), and each component content was calculated. As shown in Table 7, both enzyme reactions were conducted for 48 hours at 45° C., and the rates of AAA decrease and XXA increase were approximate equivalent for both enzymes, indicating their suitability for transesterification reaction.

Example 9

Improvement of Arachidonic Acid by Transesterification Reaction

The present inventors have developed a method for obtaining microbes capable of producing oils/fats or triglycerides containing arachidonic acid as the major constituent fatty acid and for obtaining purified oils and fats by fermentative production on an industrial scale, by culturing microbes belonging to the genus *Mortierella* (see Higashiyama et al., Enhancement of Arachidonic Acid Production by *Mortierella alpina* 1S-4, J. Am. Oil Chem. Soc., 75, pp. 1501-1505 (1998)). Using a oil/fat or triglyceride containing arachidonic acid as the main constituent fatty acid obtained by the aforementioned method as the raw material oil/fat and a deoxygenated, activated immobilized enzyme (*R. delemar* lipase) obtained by the method of Example 1, transesterification was accomplished with palm oil as a vegetable oil/fat. The oil/fat containing 40 wt % arachidonic acid as the main constituent fatty acid (250 g), palm oil (150 g) and the immobilized enzyme (40 g) were reacted at 45° C. for 48 hours. A 97% portion of the raw material oil/fat of the reaction was in triglyceride form, with arachidonic acid present as the main constituent fatty acid and tri-arachidonic acid (AAA) constituting 6.37% of the triglycerides. The oil obtained by transesterification was filtered to separate the immobilized enzyme, yielding 385 g of arachidonic acid-rich oil/fat or triglyceride containing 95.1% triglyceride, 2.83% AAA and 42.3% XXA (monoarachidonic acid having a single bonded arachidonic acid residue).

Example 10

Improvement of dihomo-γ-linolenic Acid (DGLA)-Rich Oils/Fats by Transesterification The present inventors have also developed a method for obtaining microbes capable of producing oils/fats or triglycerides containing dihomo-γ-linolenic acid (DGLA) as the major constituent fatty acid and for obtaining purified oils and fats by fermentative production on an industrial scale, by mutating microbes belonging to the genus *Mortierella* subgenus *Mortierella* (see Japanese Unexamined Patent Publication No. 5-91887). Using a oil/fat or triglyceride comprising DGLA as the main constituent fatty acid obtained by the aforementioned method as the raw material oil/fat and a deoxygenated, activated immobilized enzyme (*R. delemar* lipase) obtained by the method of Example 1, transesterification was accomplished with palm oil as a vegetable oil/fat. The oil/fat comprising 40 wt % DGLA as the main constituent fatty acid (25 g), palm oil (15 g) and the immobilized enzyme (4 g) were reacted at 45° C. for 48 hours. At the start of the reaction, triglycerides constituted 97.2%, DGLA constituted 25% of the constituent fatty acids, and tri-dihomo-γ-linolenic acid (DDD) constituted 6.09% of the triglycerides. Upon reaction, triglycerides constituted 95.3% and DDD was reduced to 3.03% of the triglycerides, and therefore the DGLA in the oil/fat comprising DGLA as the main constituent fatty acid was reduced, similar to the arachidonic acid-containing oil/fat or triglycerides.

Example 11

Preparation of Arachidonic Acid-Containing Oil/Fat (Crude Oil)

*Mortierella alpina* CBS754.68 was used as the arachidonic acid-producing strain. The preserved cells were inoculated to a 1% yeast extract, 2% glucose medium at pH 6.3, and seed culturing (first stage) was initiated at a stirring speed of 100 rpm and a temperature of 28° C. and continued for 3 days. After preparing 30 L of a 1% yeast extract, 2% glucose, 0.1% soybean oil medium at pH 6.3 in a 50 L volume submerged culturing vat, the seed culture solution (first stage) was added thereto and seed culturing (second stage) was initiated at a stirring speed of 200 rpm, a temperature of 28° C. and an internal pressure of 150 kPa, and continued for 2 days. Next, 4500 L of medium (Medium A: 270 kg soybean flour, 16.2 kg $KH_2PO_4$, 2.7 kg $MgCl_2.6H_2O$, 2.7 kg $CaCl_2.2H_2O$, 54 kg soybean oil) was sterilized at 121° C. for 20 minutes. Also, 800 L of a separate medium (Medium B: 108 kg of hydrous glucose) was sterilized at 140° C. for 40 seconds and added to the previous Medium A to prepare Medium C. After adjusting Medium C to pH 6.1, the seed culture solution (second stage) was transferred thereto to a total of 5400 L of initial culturing volume (10 kL culturing vat volume). Culturing was initiated at a temperature of 26° C., an airflow of 49 $Nm^3$/hr and an internal pressure of 200 kPa. Feeding culture was performed as shown Table 8, and the main culturing was conducted for 210 hours. After completion of the culturing, the culture solution volume was 7100 L as a result of the increase due to feeding culture and the reduction due to evaporation.

TABLE 8

Feeding culture of Example 1

| Main culturing time | Feeding Culture |
| --- | --- |
| After 19 hours | (243 kg hydrous glucose + 54 kg soybean oil)/400 L |
| After 43 hours | 243 kg hydrous glucose/400 L |
| After 67 hours | 216 kg hydrous glucose/380 L |
| After 91 hours | 162 kg hydrous glucose/300 L |
| After 120 hours | 108 kg hydrous glucose/200 L |

After completion of the culturing, sterilization was carried out at 120° C. for 20 minutes and then the wet cells were collected with a filter press and dried to a moisture content of 2 wt % using a fluidized bed drier, and a pneumatic conveyor was used to convey the dry cells to the packing location. The obtained dry cells were packed into an approximately 100 L volume aluminum pouch together with nitrogen gas, and after sealing the mouth of the bag, it was stored in a refrigerator at below 10° C.

The dry cells taken out of the container bag were subjected to extraction with hexane, and after filtering the hexane solution to remove the solid portion, it was heated under reduced pressure to remove the hexane and obtain a crude oil containing arachidonic acid as a constituent fatty acid.

Analysis of the crude oil revealed 94% triglycerides and a 29.6% arachidonic acid content of the total fatty acids.

Example 12

Transesterification of Oil Prepared in Example 11

The crude oil containing 29.6% arachidonic acid prepared in Example 11 (94% triglycerides) was subjected to lipase transesterification without addition of vegetable oil or fat, to attempt improvement of the crude oil. In immobilized lipase of *R. delemar* was used for deoxygenation and activation by the method described in Example 1, and the immobilized enzyme (4 g) was added to the crude oil containing 29.6% arachidonic acid (40 g) and reaction was conducted with shaking at 45° C. for 48 hours. The oil with a composition of 6.08% AAA and 24.15% XXA at the start of the reaction was converted to a composition of 3.21% AAA and 40.37% XXA by completion of the reaction. When the crude oil was used, it was found that the improved oil had been transesterified similar to the transesterification of oils comprising microbe-produced polyunsaturated fatty acids as the main constituent fatty acids as in Examples 6 and 8, without specific addition of vegetable oil or fat.

Example 13

Addition to Milk

A 0.44 g portion of modified oil 1 (novel transesterified oil) obtained in Example 9 was added to 100 g of powdered milk to prepare a modified milk approximating human breast milk. The modified milk comprised arachidonic acid in a proportion of 0.5% with respect to the total fatty acids.

Example 14

Addition to Butter

A 1.97 g portion of modified oil 1 (novel transesterified oil) obtained in Example 9 was added to 100 g of butter fat from which the butter milk had been removed by churning during the butter production process, and the mixture was worked to a homogeneous composition to obtain arachidonic acid-added butter.

Example 15

Addition to Juice

A 2 g portion of β-dextrin was added to 20 ml of a 20% aqueous ethanol solution, and then 100 mg of modified oil 1 (novel transesterified oil) obtained in Example 9, containing 0.05 wt % vitamin E, was added thereto while stirring with a stirrer, and the mixture was incubated at 50° C. for 2 hours. After cooling to room temperature (approximately 1 hour), incubation was continued at 4° C. for 10 hours while continuing to stir. The produced precipitate was recovered by centrifugal separation, and after washing with n-hexane, it was lyophilized to obtain 1.8 g of a cyclodextrin clathrated compound comprising arachidonic acid-containing triglycerides.

A 1 g portion of this powder was uniformly mixed with 10 L of juice to prepare juice comprising arachidonic acid-containing transesterified oil.

Example 16

Preparation of Triglycerides Containing Medium-Chain Fatty Acids and Arachidonic Acid in the Same Molecule by Transesterification, and Purification of the Oil/Fat The immobilized lipase prepared by the method of Example 1 was subjected to deoxygenation and activation according to Example 1. Specifically, triglyceride contains 40% arachidonic acid (SUNTGA40S, trade name of Suntory Co., Ltd.) (200 g), MCT (COCONARD RT, trade name of Kao Corp.) (200 g), the aforementioned immobilized lipase (40 g) and water (8 ml) were placed in a sealable bottle and subjected to the deoxygenation and enzyme activation procedure described in Example 1.

The oil used for the activation procedure was removed, and then SUNTGA40S (200 g) and MCT (200 g) were freshly added to the immobilized enzyme-containing bottle prior to shaking at 30° C. for 48 hours (100 rpm).

After completion of the reaction, the oil was taken out from the bottle and the triglycerides of the transesterified oil were analyzed by the HPLC described in Example 3. The analysis results are shown in Table 9. The HPLC method does not allow separate analysis of triglycerides containing medium-chain fatty acids and arachidonic acid (for example, triglycerides with octanoic acid at positions 1,2 and arachidonic acid at position 3 (88A), triglycerides with octanoic acid at positions 1,3 and arachidonic acid at position 2 (8A8), etc.) obtained by transesterification. This was therefore combined with GC (conditions shown below) analysis for separate analysis of 88A and 8A8. 88A appeared on the chromatograph at 17.01 minutes, and 8A8 at 17.15 minutes.

The content of each triglyceride resulting from the reaction was as shown in Table 10.

[GC Analysis Method]
Column: Frontier Ultra ALLOY UA-17-15M-0.1F (15 m×0.25 mm×0.1 μm)
Column temperature: 260° C.-(1° C./min)-290° C.-(10° C./min)-390° C. (5 min)
Analysis time: 45 minutes
Injection port temperature: 310° C.
Detector temperature: 370° C. (Hydrogen ionization detector)
Carrier gas: helium
Line speed: 40 cm/min
Sample: Injection of 1 μl of 1% solution of oil (triglyceride) dissolved in hexane The transesterified oil remaining after analysis was subjected to molecular distillation to remove approximately 85% of the MCTs remaining after the reaction.

TABLE 9

| Triglyceride | Proportions of triglycerides Results of HPLC analysis | |
|---|---|---|
| | Before reaction (wt %) | After reaction (wt %) |
| 8A8, etc. | 0.00 | 15.87 |
| 8P8 | 0.00 | 6.96 |
| 8L8 | 0.00 | 6.58 |
| 8O8 | 0.00 | 15.23 |
| AAA | 4.84 | 1.67 |
| 8AA | 0.00 | 6.25 |
| GAA | 0.79 | 0.00 |
| LAA | 3.06 | 2.86 |
| PAA | 5.55 | 4.71 |
| SAA | 3.97 | 1.45 |
| C22AA | 1.30 | 0.28 |
| C24AA | 3.72 | 0.52 |
| LLA | 0.55 | 1.45 |
| PGA | 1.88 | 0.91 |
| OLA | 0.67 | 0.28 |
| PLA | 3.04 | 1.01 |
| OOA | 0.60 | 0.00 |
| POA | 2.97 | 0.84 |
| PPA | 1.32 | 0.41 |
| SOA | 0.90 | 0.70 |
| PSA | 1.30 | 0.23 |
| SSA | 0.93 | 0.44 |
| LAC22 | 0.57 | 0.27 |
| 888 | 50.00 | 23.27 |
| Other triglycerides | 12.04 | 7.81 |

8A8, etc.: Mixture of 8A8 (88A, 8A8), 8G8, 8D8

The fatty acids were indicated by alphanumeric notation (without specifying the binding position on the glycerin backbone). (The glycerin backbone positions of the triglycerides other than 88A and 8A8 in the table are not specified in the table.)

Fatty Acid Notations:
8: octanoic acid, A: arachidonic acid, D: DGLA, P: palmitic acid, S: stearic acid, O: oleic acid, G: γ-linolenic acid, L: linoleic acid, C22: $C_{22}$ saturated linear fatty acid, C24: $C_{24}$ saturated linear fatty acid

TABLE 10

| Triglyceride | Proportions of triglycerides Results of GC and HPLC analysis | |
|---|---|---|
| | Before reaction (wt %) | After reaction (wt %) |
| 88A | 0.00 | 8.36 |
| 8A8 | 0.00 | 5.37 |
| 88G + 8G8 | 0.00 | 0.35 |
| 88D + 8D8 | 0.00 | 1.79 |
| 88L + 8L8 | 0.00 | 6.58 |
| 88P + 8P8 | 0.00 | 6.96 |
| 88O + 8O8 | 0.00 | 15.23 |
| 8AA + A8A | 0.00 | 6.25 |
| AAA | 4.84 | 1.67 |
| XAA + AXA | 18.39 | 9.82 |
| XXA + XAX | 14.73 | 6.54 |
| 888 | 50.00 | 23.27 |
| Other triglycerides | 12.04 | 7.81 |

The triglycerides are represented by their constituent fatty acid types, with the binding positions of each fatty acid shown in this table in the order 1,2,3 or 3,2,1. The 2-position of glycerin in a triglyceride is an asymmetric carbon, and therefore the 1- and 3-positions are sterically different in the strict sense. However, as the 1- and 3-positions are basically equivalent in physiological terms as evidenced by recognition by lipases, triglycerides are considered the same even if both end positions are switched around the center fatty acid (position 2).

Explanation of Notations in Table
  Fatty acids represented alphanumerically.
  Fatty Acid Notations:
    8: octanoic acid, A: arachidonic acid, D: DGLA, P: palmitic acid, S:
  stearic acid, O: oleic acid, G: γ-linolenic acid, L: linoleic acid, C22: $C_{22}$ saturated linear fatty acid, C24: $C_{24}$ saturated linear fatty acid
  XAA+AXA: Total of GAA, LAA, PAA, SAA, C22AA, C24AA
  XXA+XAX: Total of LLA, PGA, OLA, PLA, OOA, POA, PPA, SOA, PSA, SSA, LAC22
  The fatty acid binding positions of specific triglycerides (for example, PGA) represented by XAA or XXA are not specified. The specific contents are shown in Table 9.

The invention claimed is:

1. A transesterified composition containing at least 20% of polyunsaturated fatty acids containing 20-24 carbons and two to six double bonds, and which contains at least 40% of triglycerides with one residue of a polyunsaturated fatty acid containing 20-24 carbons and two to six double bonds in the molecule, and no more than 4.0% of triglycerides with 3 residues of the same polyunsaturated fatty acid containing 20-24 carbons and two to six double bonds.

2. The transesterified composition according to claim 1, which contains at least 20% of fungus-produced ω6 series polyunsaturated fatty acids containing 20-24 carbons and two to six double bonds, and which contains at least 40% of triglycerides with one residue of ω6 series polyunsaturated fatty acids containing 20-24 carbons and two to six double bonds in the molecule, and no more than 4.0% of triglycerides with 3 residues of the same fungus-produced ω6 series polyunsaturated fatty acids containing 20-24 carbons and two to six double bonds.

3. The transesterified composition according to claim 1, which contains at least 20% of fungus-produced ω9 series polyunsaturated fatty acids containing 20-24 carbons and two to six double bonds, and which contains at least 40% of triglycerides with one residue of ω9 series polyunsaturated fatty acids containing 20-24 carbons and two to six double bonds in the molecule, and no more than 4.0% of triglycerides with 3 residues of the same fungus-produced ω9 series polyunsaturated fatty acids containing 20-24 carbons and two to six double bonds.

4. The transesterified composition according to claim 1, containing at least 20% of arachidonic acid, and which contains at least 40% of triglycerides with one residue of arachidonic acid in the molecule and no more than 4.0% of AAA, wherein AAA is a triglyceride with 3 residues of arachidonic acid in the molecule.

5. The transesterified composition according to claim 1, containing at least 20% of dihomo-γ-linolenic acid, and which contains at least 40% of triglycerides with one residue of dihomo-γ-linolenic acid in the molecule and no more than 4.0% of DDD, wherein DDD is a triglyceride with 3 residues of dihomo-γ-linolenic acid in the molecule.

6. The transesterified composition according to claim 1, containing at least 20% of mead acid, and which contains at least 40% of triglycerides with one residue of mead acid in the molecule and no more than 4.0% of MMM, wherein MMM is a triglyceride with 3 residues of mead acid in the molecule.

7. A human nutritive composition comprising the transesterified composition according to claim 1.

8. A food composition comprising the transesterified composition according to claim 1.

9. The food composition according to claim 8, characterized in that the food composition is a functional food, nutritional supplement food, modified milk for premature infants, modified milk for infants, infant food, maternal food, or geriatric food.

10. An animal feed comprising the transesterified composition according to claim 1.

* * * * *